United States Patent [19]
Atkinson et al.

[11] Patent Number: 5,196,020
[45] Date of Patent: Mar. 23, 1993

[54] COMB FOR USE WITH SKIN GRAFT PREPARATION APPARATUS

[75] Inventors: Robert W. Atkinson, Dover; John P. McDougall, Strasburg; William J. Donizetti, Dover, all of Ohio

[73] Assignee: Zimmer, Inc., Warsaw, Ind.

[21] Appl. No.: 767,728

[22] Filed: Sep. 30, 1991

[51] Int. Cl.$^5$ .............................................. A61B 19/00
[52] U.S. Cl. ........................... 606/132; 606/1; 606/131; 452/75; 452/82; 452/125; 452/127; 452/132
[58] Field of Search ............... 606/1, 131, 132; 452/75, 82, 125, 127, 132

[56] References Cited

U.S. PATENT DOCUMENTS

| | | | |
|---|---|---|---|
| 1,516,071 | 11/1924 | Apolant | 606/132 |
| 1,842,534 | 1/1932 | Brill | 606/132 |
| 2,484,740 | 10/1949 | Reese | 606/1 |
| 2,579,029 | 12/1951 | Barker et al. | 606/132 |
| 3,412,732 | 11/1968 | Simon | 606/132 |
| 3,640,279 | 2/1972 | Brown et al. | |
| 4,537,207 | 8/1985 | Gilhaus | 606/131 |
| 5,004,468 | 4/1991 | Atkinson | 606/132 |

FOREIGN PATENT DOCUMENTS

| | | | |
|---|---|---|---|
| 0733330 | 5/1966 | Canada | 606/132 |
| 1532005 | 12/1989 | U.S.S.R. | 606/131 |

*Primary Examiner*—Stephen C. Pellegrino
*Assistant Examiner*—Glenn K. Dawson
*Attorney, Agent, or Firm*—Todd A. Dawson

[57] ABSTRACT

A comb for connection to the skin meshing unit adjacent the cutter blades to contact the blades to remove the skin from the blades. The comb includes a plurality of slots which accommodates a portion of the cutter blades as the blades rotate through the skin sample passed under the blades. Each longitudinal end of the slot includes angled side wall and is bevelled relative to the bottom wall of the comb to form a V-shaped groove which engages the cutting edge of the blades in close contact to remove the skin from the cutter.

1 Claim, 3 Drawing Sheets

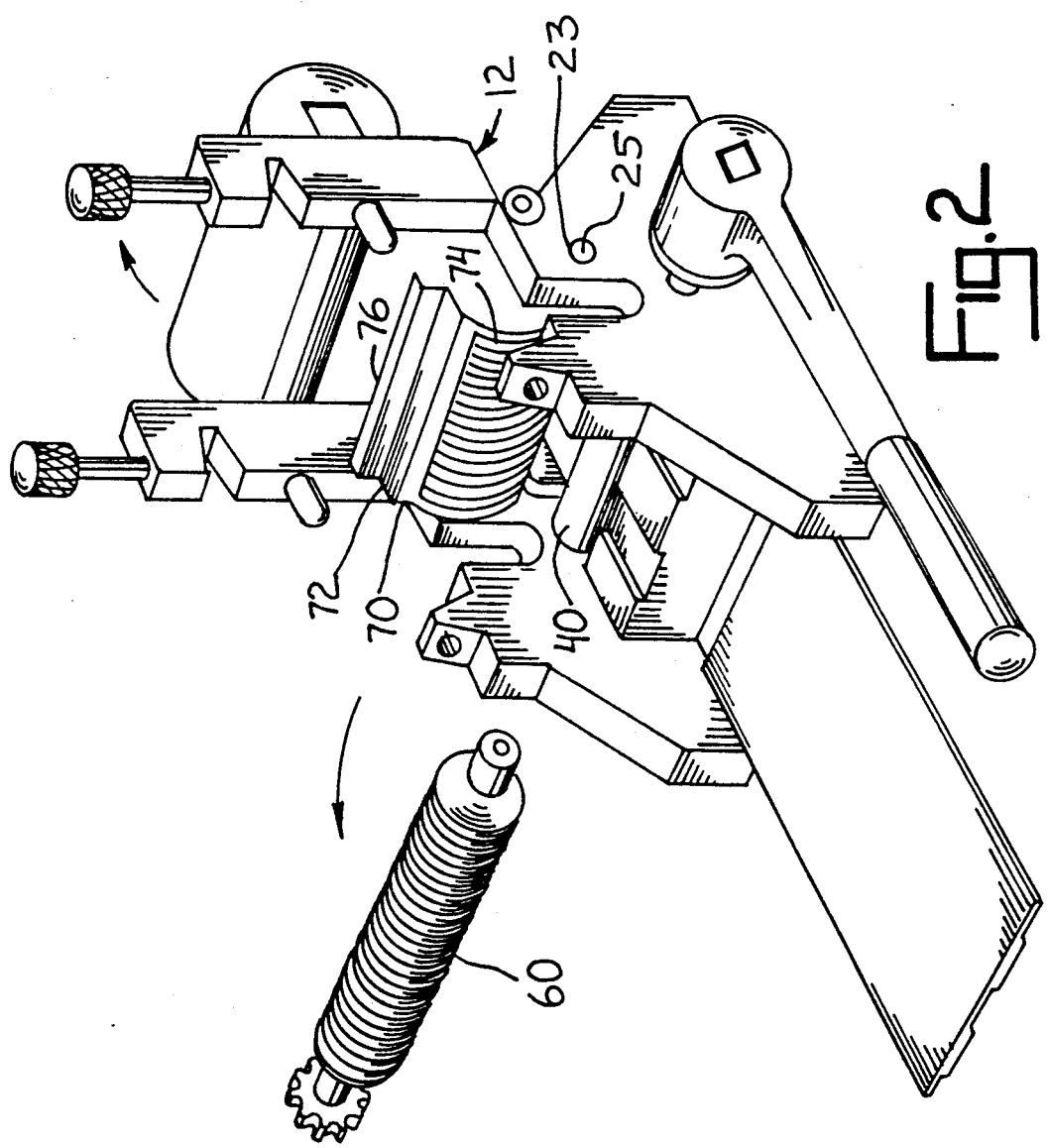

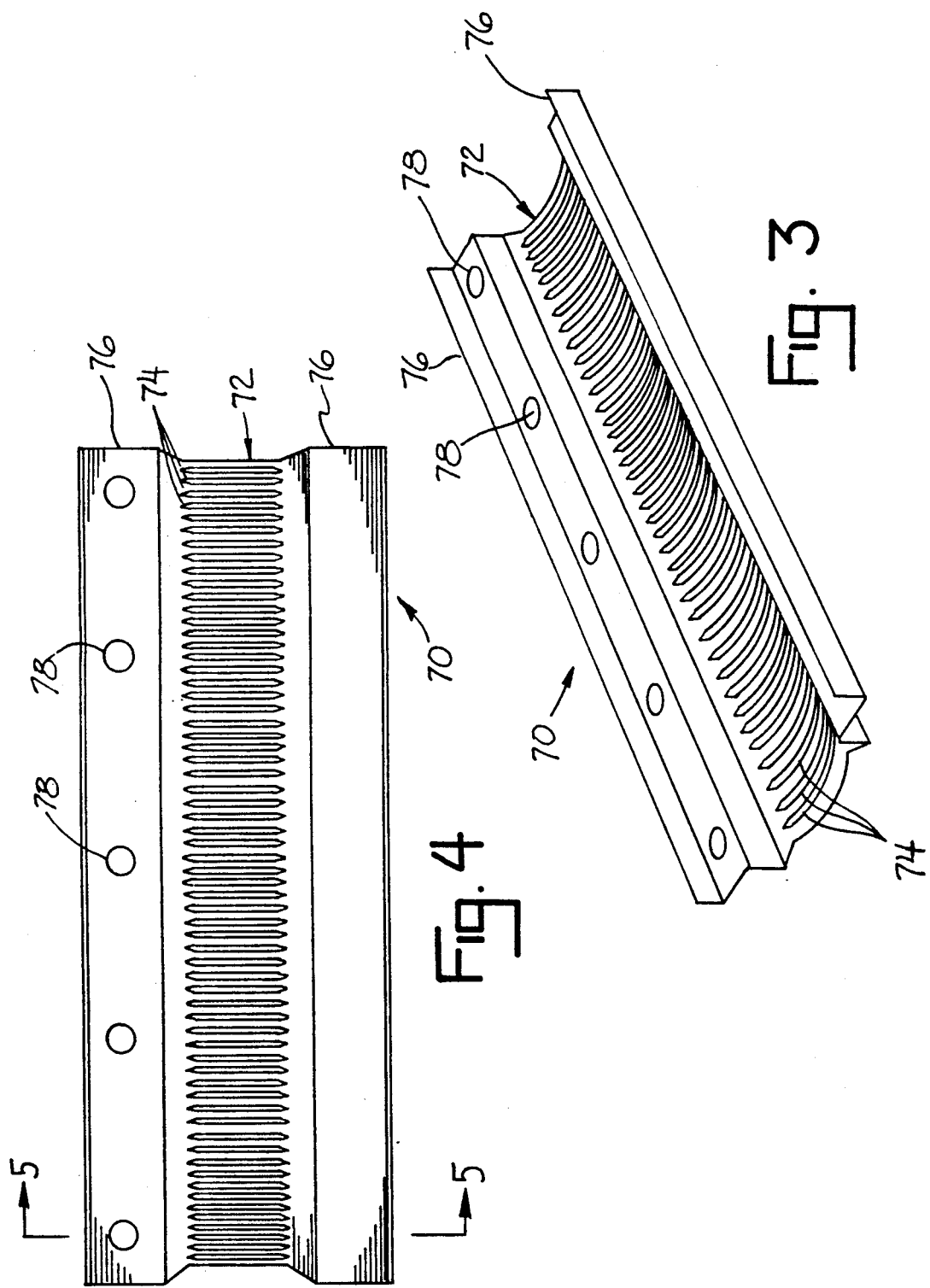

COMB FOR USE WITH SKIN GRAFT PREPARATION APPARATUS

FIELD OF THE INVENTION

This invention relates to the field of skin graft preparation and relates particularly to a comb device for connection to a skin graft preparation device to remove the skin from the cutter blades.

BACKGROUND OF THE INVENTION

Skin graft harvesting and meshing is widely known in the art for preparing a section of a patient's skin for grafting. Numerous patents have issued and articles have been written discussing the benefits and the desirability of meshing the graft to increase its coverage. One such skin graft preparation apparatus is disclosed in U.S. Pat. No. 5,004,468 incorporated herein by reference.

During the preparation or meshing procedure, the skin may stick to the cutter blades requiring the surgeon to physically remove the skin from the blades. This method of removal is cumbersome and costly in terms of time and in terms of the increased chances of damage to the skin sample.

SUMMARY OF THE INVENTION

This invention eliminates the problems discussed above by providing a comb device connected to the skin meshing unit adjacent the cutter blades to contact the blades to remove the skin from the blades. The comb includes a plurality of slots which accommodates a portion of the cutter blades as the blades rotate through the skin sample passed under the blades. Each longitudinal end of the slot includes angled side wall and is bevelled relative to the bottom wall of the comb to form a V-shaped groove which engages the cutting edge of the blades in close contact to remove the skin from the cutter.

Accordingly, it is an object of this invention to provide for a novel comb for a skin preparation device.

Another object of this invention is to provide for a comb for a skin preparation device having a plurality of slots for accommodating the cutters of the preparation device.

Another object of the invention is to provide for a comb for a skin preparation device wherein the slots include bevelled and angled end walls to engage the cutters of the device in scraping contact.

Still other objects of the invention will become apparent upon a reading of the following description taken with the accompanying drawings.

BRIEF DESCRIPTION OF THE DRAWINGS

FIG. 2 is a perspective view of the device of FIG. 1 with the preparation device opened to expose the cutter and comb.

FIG. 3 is a perspective view of the comb of the invention.

FIG. 4 is an elevational view of the comb of the invention.

DESCRIPTION OF THE PREFERRED EMBODIMENT

The preferred embodiment herein described is not intended to be exhaustive or to limit the application to the precise forms disclosed. Rather, they are chosen and described in order to best explain the invention so that others skilled in the art might utilize it teachings.

Figure 1:
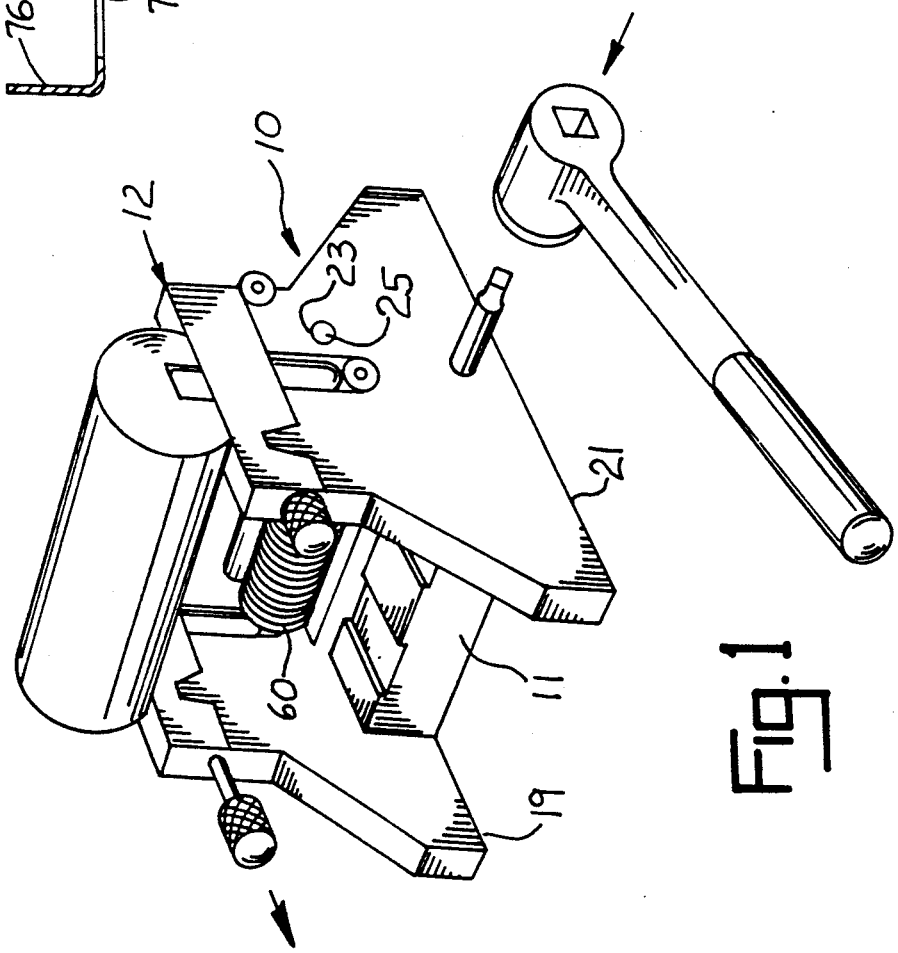
FIG. 1 is a perspective view of a skin graft preparation device with the comb of the invention.

A skin meshing apparatus 10 is illustrated in FIGS. 1 and 2 as including, a base 11 having a pair of opposed supports 19, 21 connected thereto. Supports 19, 21 include a pair of aligned openings to rotatably receive the guide roller 40 and cutter roller 60. Cutter roller 60 may be removed form supports 19, 21 by pivoting open the cover 12. A carrier is provided to support the skin sample as the carrier and sample is passed between the guide roller 40 and cutter roller 60 to mesh the skin. A more detailed description of the construction and operation of the basic meshing apparatus may be had by a reading of U.S. Pat. No. 5,004,468 incorporated herein by reference.

The comb 70 of the invention is best illustrated in FIGS. 3-6 and includes an elongated body 72 having a plurality of transverse slots 74 therethrough. A flange 76 extends from each side edge of the body in a manner illustrated in the figures. Comb 70 is preferably formed from a single piece of material, preferably metal. Body 72 is formed having a gentle arc between flanges 76. A plurality of openings 78 are formed through one flange 76. Comb 70 is pivotally connected to supports 19, 21 by a bar connected between the supports and extending into openings 23 (only one shown) of the support posts. Fasteners (not shown) traverse the openings 78 and seat within the bar to connect the comb to the bar. In the preferred embodiment the bar 25 is pivotally connected between the supports such that with the comb connected thereto by common fasteners, the comb is pivotable relative to the supports. Although the comb is described as being connected to the bar (not shown) which is pivotally connected to the supports, any suitable means for pivotally connecting the comb to the supports is acceptable. With cover 12 in the open position of FIG. 2 the comb may be pivoted upwardly as shown in FIG. 2 for cleaning. In use, the cutter is seated within the comb such that the teeth of the cutter pass through the slots of the comb.

Figure 5:
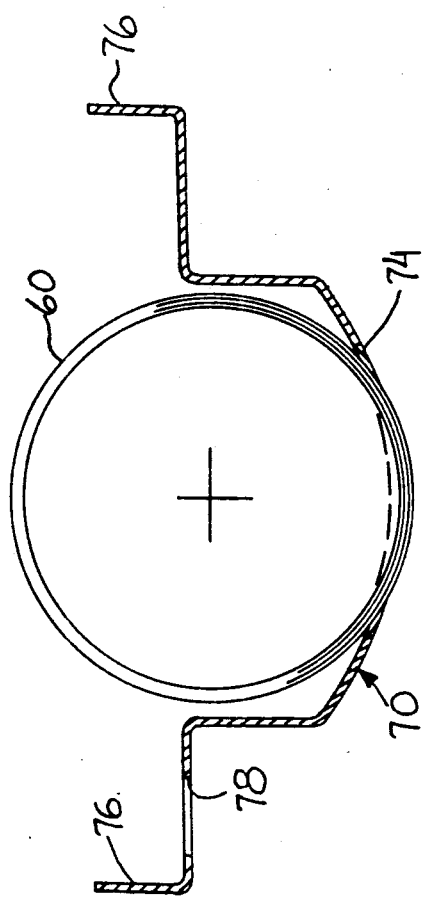
FIG. 5 is a cross sectional view of the comb of the invention taken from line 5—5 of FIG. 4 with a cutter roller shown for illustrative purposes.
Figure 6:
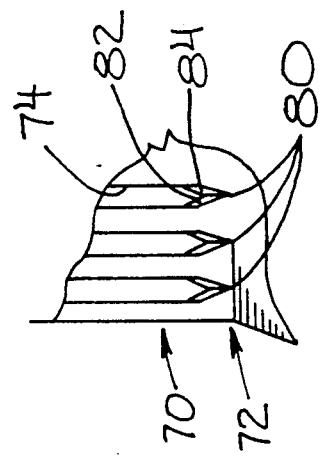
FIG. 6 is an enlarged view of the area circles in FIG. 4 and designated by numeral 6.

As best illustrated in FIG. 5, each slot terminates in a converging or pointed ends 80. As shown in the sectional view of FIG. 5, the end of each slot is beveled relative to the body 72 forming converging faces 82, 84. In use, as the cutter is rotated and the skin sample is passed between the guide roller and the comb, the blades of the cutter cut the skin sample in the desired pattern. As explained earlier, when a skin sample is cut, the sample has a tendency to adhere slightly to the cutter blade. Since, the edge walls of the slots are in close proximity to the individual cutter blades, the comb body contacts the skin to remove the skin from the blades and press the skin against the carrier. The bevelled end walls are formed to substantially match the contour or the cutter blades.

I claim:

1. A one piece comb for connection to a skin preparation device, said skin preparation device including a plurality of cutting blades for cutting into a sample of skin, said one-piece comb including a body having a flange extending therefrom said body also including a plurality of slots therethrough adapted to accomodate said blades such that a portion of said blades pass through said body for cutting engagement with said skin sample passing between said one-piece comb and said blades, said plurality of slots each terminating in a converging V-shaped end, said flange being configured for pivotal connection to said skin preparation device, said comb constituting means for removing portions of said skin sample from said cutter blades wherein said V-shaped ends of said slots are configured to substantially match a converging cutting surface of said blades, said comb being pivotable about said flange between a generally horizontal use position and a generally vertical cleaning position.

* * * * *